United States Patent [19]
Kadowaki et al.

[11] Patent Number: 5,578,281
[45] Date of Patent: Nov. 26, 1996

[54] CASH TRANSACTION MACHINE

[75] Inventors: Minoru Kadowaki, Toyota; Atsuko Mizoguchi, Owariasahi; Ryozo Nakamura, Aichi-ken; Riichi Kato, Owariasahi; Kousuke Noda, Tsuchiura; Hiroyuki Kashiwada, Nagoya, all of Japan

[73] Assignee: Hitachi, Ltd., Tokyo, Japan

[21] Appl. No.: 297,093

[22] Filed: Aug. 26, 1994

[30] Foreign Application Priority Data

Aug. 27, 1993 [JP] Japan .................... 5-212487
Dec. 16, 1993 [JP] Japan .................... 5-316267

[51] Int. Cl.⁶ .............. D21H 21/36; A61L 2/04; G06F 15/30
[52] U.S. Cl. .............. 422/307; 235/379; 235/7 R; 134/122 R
[58] Field of Search ................... 422/5, 24, 307, 422/304, 291, 300; 235/7 R, 379; 134/122 R

[56] References Cited

U.S. PATENT DOCUMENTS

| 579,124 | 3/1926 | MacGrath | 235/7 R |
|---|---|---|---|
| 3,779,791 | 12/1973 | Ploetz et al. | 21/58 |
| 4,449,050 | 5/1984 | Kamhi | 250/455.1 |
| 4,697,071 | 9/1987 | Hiraoka et al. | |
| 4,972,958 | 11/1990 | Ito et al. | |
| 5,021,639 | 6/1991 | Hura et al. | |
| 5,326,542 | 7/1994 | Sizer et al. | 422/291 |
| 5,374,814 | 12/1994 | Kako et al. | 235/379 |

FOREIGN PATENT DOCUMENTS

| 47-45997 | 12/1972 | Japan . |
|---|---|---|
| 49-24194 | 3/1974 | Japan . |
| 62-42296 | 2/1987 | Japan . |
| 47260 | 2/1988 | Japan . |
| 58124873 | 2/1988 | Japan . |
| 63-66059 | 3/1988 | Japan . |
| 92566 | 4/1988 | Japan . |
| 63-112350 | 5/1988 | Japan . |
| 63-92566 | 5/1988 | Japan . |

Primary Examiner—N. Bhat
Attorney, Agent, or Firm—Antonelli, Terry, Stout & Kraus

[57] ABSTRACT

A cash transaction machine performs receiving and/or paying transactions of bills by manipulation of a user, transfers bills between a receptacle where bills are paid in and out and a storage where bills are stored, and by using a sterilizing unit for heat-sterilizing bills being transferred, detects the temperature of the sterilizing unit with a temperature detector, controls the temperature of the sterilizing unit so as to be in a specified temperature range, and also controls the processing of transactions by, for example, temporarily stopping the transaction according to the detected temperature.

49 Claims, 12 Drawing Sheets

CASH TRANSACTION MACHINE

CROSS-REFERENCE TO RELATED APPLICATION

Ser. No. 07/637,785 (Jan. 7, 1991), now U.S. Pat. No. 5,374,814 issued Dec. 20, 1994, entitled Cash Transaction Machine and Method with Money Disinfection is a related application of the present application and it is incorporated herein by reference.

BACKGROUND OF THE INVENTION

This invention relates to a cash transaction machine for depositing and withdrawing by the user's manipulation, and more particularly to a cash transaction machine with a function to sterilize or disinfect bills.

A cash transaction machine having a function to sterilize bills is disclosed in JP-A-3-209595, in which sterilization methods by heat, ultraviolet rays, chemicals are revealed. In sterilizing bills by heat sterilization, a method of heating a bill with heating means provided on the transport path is effective. Heat sterilization of bills, such as this, is shown in JP-A-4-114652. In JP-A-4-114652, there is provided a heat sterilizing section, which includes a heating roller containing heating means such as a heater provided on the transport path, and a heat-resistant belt wrapping around the heating roller. Bills are moved between the heating roller and the heat-resistant belt as they are transferred on the transport path, and the bills are heat-sterilized at the bill-holding section including the heating roller and the heat-resistant belt.

In a heat sterilization process in which the heating roller and the heat-resistant belt are raised to a high temperature and while a bill is passed between the heating roller and the heat-resistant belt, the bill is sterilized by heat. The temperature of the bill is at about room temperature at most before it comes in between the heating roller and the heat-resistant belt, and in order to raise the bill at this temperature to a sterilizable temperature while the bill is placed between the heating roller and the heat-resistant belt, a large quantity of heat is required. When bills are sterilized successively, the heating roller and the heat-resistant belt are deprived of a considerable quantity of heat in a short time, so that the temperature of the heating roller and the heat-resistant belt fall rapidly. Not only being deprived of heat by the bills, the heating roller and the heat-resistant belt themselves are radiating heat. Therefore, for heating the heating roller and the heat-resistant belt by the heating means during sterilization, it is necessary to provide a large capacity heat source to supply a quantity of heat equivalent to the deprived quantity of heat. However, it is difficult to install a large capacity heat source for reasons of power consumption, installation space, or the like. An important problem is how to maintain the heating roller and the heat-resistant belt at a sterilizing temperature.

By the examination of the germs on the circulating bills, the present inventors found that various kinds of germs, including *staphylococcus aureus* and bacillus subtilis adhere to the bills in circulation. Experimental research has been made into the heating condition for thermally killing the microbes including those mentioned above. To give an example, according to "Principal Sterilization and Disinfection in Practice-revised edition -" (issued by Nihon Iji Shimposha, Jul. 31, 1989), the sterilizing condition is 5 to 10 min at 60° C. for *staphylococcus aureus*, and 15 min at 104° C. for *bacillus subtilis*.

However, in a bill handling machine, when a bill heating section is provided along the transport path and bills are transferred and sterilized one after another, because this kind of machine transfers 7 to 12 bills in one second at the speed of about 1 m per second, even if the heating section is prolonged, the heating time that can be secured is 0.05 to 0.15 s at most, which does not satisfy the heating time as one of the sterilizing conditions mentioned above.

It is known that in the dying process of those germs, if the heating condition is fixed, the number of dead germs increases exponentially. As the heating time is reduced, the germicidal effect is decreased.

Therefore, in a bill handling machine, if a bill heating section is provided on the transport path and the bills which are transferred are sterilized one after another, when the heating time is so short as 0.05 to 0.15 s as mentioned above, by setting a higher heating temperature than in the above-mentioned literature, it is possible to obtain powerful germicidal effects. On the other hand, If the temperature of the heating roller and the belt is raised too high, problems deriving from the machine construction arise such as an increase in heat quantity produced, and danger of smoke generation and catching fire.

Meanwhile, in putting into practical application the sterilizing mechanism in the bill handling machine, it is not necessary to offer such a high germicidal effect as in sterilizing equipment used in medical scenes because a user touches a sterilized bill with his or her contaminated hand in daily life and not a few germs again adhere to the bill while it is stored in the purse. With this taken into consideration, the heating condition should be set.

SUMMARY OF THE INVENTION

An object of the present invention is to provide a bill sterilizing unit that can be mounted in an conventional automatic cash transaction machine and a cash transaction machine that can ensure an effective germicidal effect.

An automatic cash transaction machine according to the present invention comprises a receptacle for putting in and taking out bills, a bill storage box for storing bills, transporting means for transporting bills between the receptacle and the bill storage box, sterilizing means for transferring bills to and from the transporting means and sterilizing the bills by heat, temperature detecting means for detecting the temperature of the sterilizing means, and control means for controlling the bill heating temperature of the sterilizing means so as to be in a specified temperature range in response to the temperature detected by the temperature detecting means and controlling transactions according to the temperature.

The present invention controls the sterilizing means under the condition that more than 90% of *staphylococcus aureus* adhering to bills are killed. In other words, the heating temperature and time by the sterilizing means are controlled so as to be 140° C. or higher and 0.05 to 0.15 s, respectively. The bills are heated while they are moving through the heating section, and more than 90% of *staphylococcus aureus* adhering to the bills are destroyed, which is sufficiently hygienic for daily life.

If the number of bills to be sterilized continuously is limited to a number at which the heating temperature does not fall below a specified temperature, it is possible to continuously sterilize less than a certain number of bills. By arranging for the number of bills that can be sterilized continuously to be more than the number of bills deposited or withdrawn in one transaction, bills can be sterilized securely without affecting transactions.

DESCRIPTION OF THE PREFERRED EMBODIMENTS

Embodiments of the present invention will be described with reference to the accompanying drawings.

Figure 1:
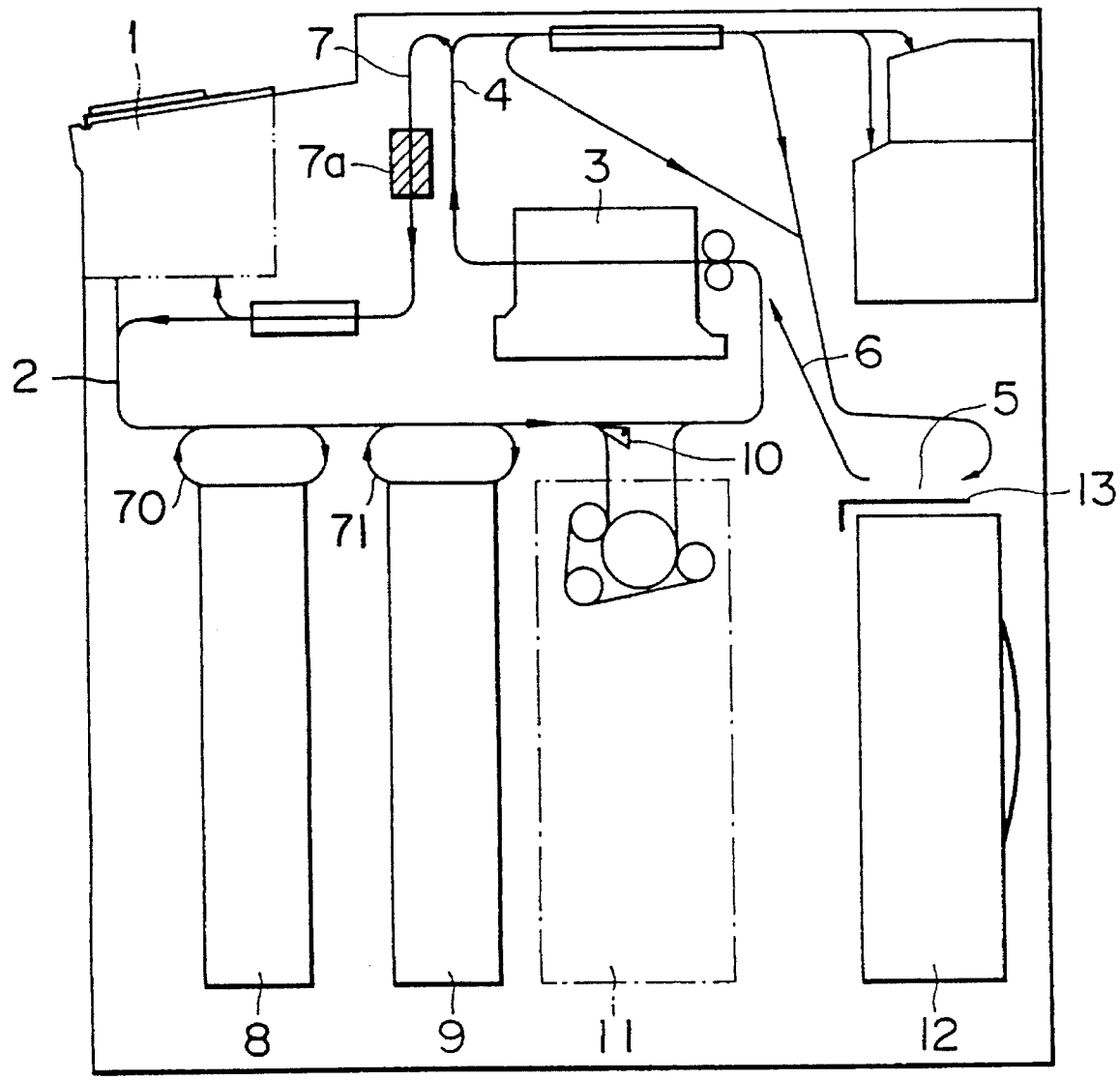
FIG. 1 is a diagram showing an embodiment of the present invention.

FIG. 1 shows a cash transaction machine as an embodiment of the present invention.

In a money receiving transaction, the user puts bills into a receptacle 1. The bills put in are separated from one another by a separating mechanism, not shown, in the receptacle 1, and are transferred on the transport path to a discriminator 3. The discriminator 3 discriminates the bills in terms of denomination, counterfeit or not, neat or damaged, and the number. The bills are further transferred through the transport path 4, and stacked in a temporary accumulation mechanism 5. If the transaction that the user performed is concluded, the bills are separated by a separating mechanism, not shown, transferred from the temporary accumulation mechanism 5 back to the discriminator 3 for discrimination, and passing through the transport paths 4, 7 and 2, sent to denomination boxes 8, 9 and stored classified by denomination, with which the money receiving transaction is finished. The denomination box 8 stores 1000-yen bills, and the denomination box 9 stores 10000-yen bills, for example.

In a money paying transaction, bills as many as the user requires from the denomination boxes 8, 9 are separated from one another by a separating mechanism, not shown, and sent onto the transport path 2 by a bill transfer means shown schematically by the lines with arrows, 70 and 71, in FIG. 1. A gate 10 is installed on the midway of the transport path 2. In a money paying transaction, the gate 10 is switched to the side of the sterilizing/disinfecting unit 11, and the bills are transferred to the sterilizing/disinfecting unit 11 where they are sterilized or disinfected. After sterilized or disinfected by the sterilizing/disinfecting unit 11, the bills are passed through the transport paths 2, 4 and 7, stacked in the receptacle 1 and dispensed, with which the money paying transaction is finished. The sterilizing/disinfecting unit 11 carries on heat sterilization, which will be described later, and the bills stacked in the receptacle 1 may sometimes be hot. Therefore, a bill cooling unit 7a may be installed on the transport path 7 to cool the bills heat-sterilized by the sterilizing/disinfecting unit 11 so as not to give the user a feeling of discomfort. There is provided a part of the transport path to detour the bills around the sterilizing/disinfecting unit 11, This is effected by switching over the gate 10, so that the bills are detoured past the sterilizing/disinfecting unit 11.

When the supply of bills in the denomination boxes 8, 9 is running short, the denomination boxes 8, 9 are replenished with bills from a bill cassette 12. In other words, since the bill cassette 12 is detachable, a clerk in charge sets bills in the bill cassette 12. After the separator 13 is withdrawn, the bills are sent out of the cassette 12 by a separating mechanism, not shown, and are sent through the transport path 6 to the discriminator 3, which discriminates the bills of different denominations and counts the bills. Then, the bills of different denominations are separately replenished or filled in the respective denomination boxes. The temporary accumulation mechanism 5, the bill cassette 12, and the separator 13 may be constructed as shown in JP-A-62-42296, for example.

When either of the denomination boxes 8, 9 becomes full, the bills are sent out of the full denomination box 8 or 9, and after the discriminator 3 finishes the discrimination and counting of the bills of different denominations, the bills are brought back in the cassette 12. Or, all bills may be recovered from the denomination boxes 8, 9 and counted by the discriminator 3 to carefully examine the quantity of bills present in the machine. Moreover, by moving the bills sequentially through the discriminator 3 when they are sent to the denomination boxes 8, 9 or the bill cassette 12, the quantity of bills present in the machine can be counted for careful examination. In the above recovery for examination, too, by switching the gate 10 of the transport path 2, the bills can be sterilized or disinfected.

Figure 6:
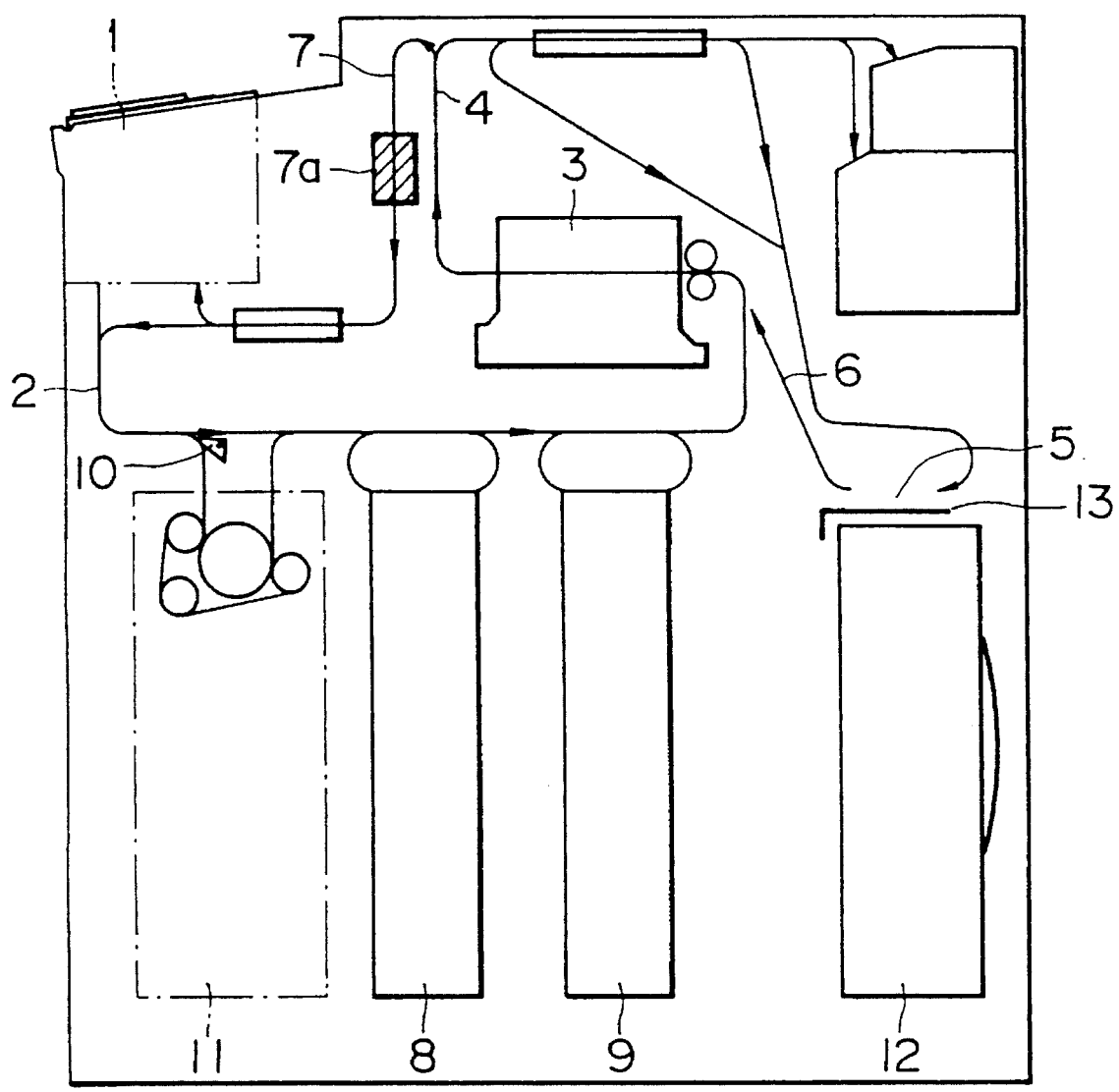
FIG. 6 is another embodiment of the present invention in which the sterilizing/disinfecting section is installed in the deposit route and the loading route.

FIG. 6 shows an embodiment in which the sterilizing/disinfecting unit 11 is provided on the upstream side of the denomination boxes 8, 9 on the transport path 2. In the construction in FIG. 6, the bills can be sterilized or disinfected in the money receiving transaction, or bill replenishing or loading operations. In the construction in FIG. 6, the sterilization or disinfection process is not performed in the money paying transaction.

The money receiving transaction includes a money receiving process for accumulating bills that the user throws in the receptacle 1 into the temporary accumulation mechanism 5 and a received money counting process for storing bills from the temporary accumulation mechanism 5 into the denomination boxes 8, 9. In the money receiving process, the bills thrown in to the receptacle 1 are sent one after another onto the transport path 2, and after passing through the transport path 2, the discriminator 3 and the transport path 4, the bills are stacked in the temporary accumulation mechanism 5. The received money counting process starts when as the result of the money receiving process the transaction is concluded by obtaining the user's confirmation. The bills stacked in the temporary accumulation mechanism 5 are sent one after another onto the transport path 6, and passed through the discriminator 3, and the transport paths 4, 7 and 2. From the transport path 2, the bills are sent through the gate 10 to the sterilizing/disinfecting unit 11. After being sterilized or disinfected, the bills are again sent to the transport path 2, and stored in the denomination boxes 8, 9 provided on the downstream side of the transport path 2.

Figure 2:
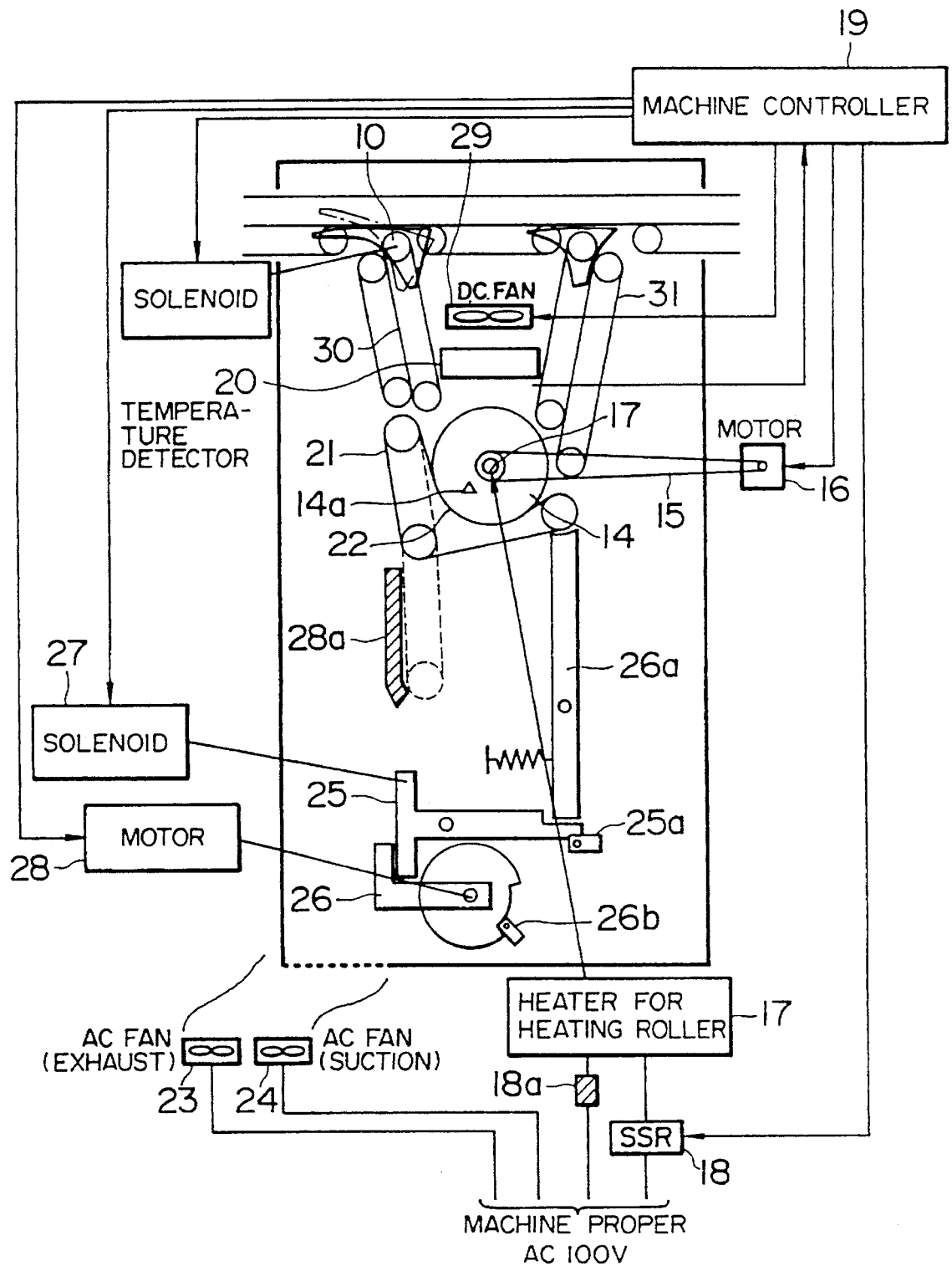
FIG. 2 is a diagram showing the construction of a sterilizing/disinfecting section for sterilization or disinfection.
Figure 3:
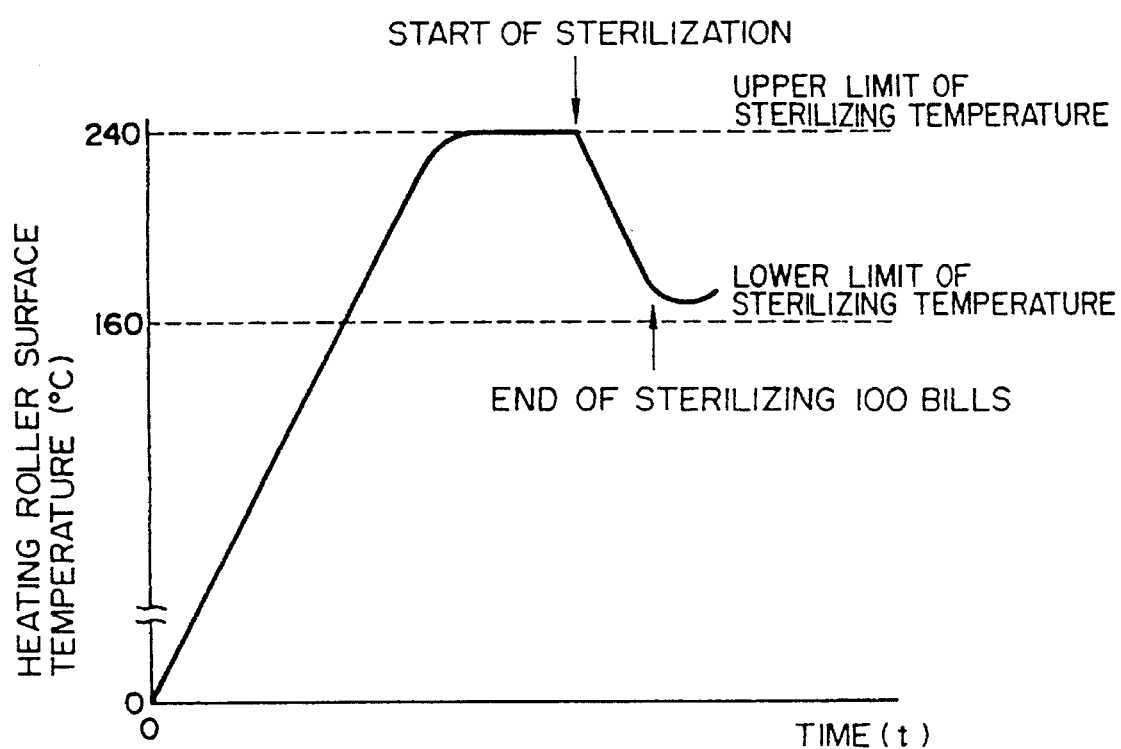
FIG. 3 is a diagram showing temperature changes of the sterilizing section.

With reference to FIG. 2, description will be made of the sterilizing/disinfecting unit 11 in the cash transaction machine shown in FIGS. 1 and 6. FIG. 2 shows the construction of the bill sterilizing/disinfecting unit 11.

Reference numeral 14 denotes a sterilizing means in the form of a metal heating roller for heat sterilizing the bills, which is supported by a bearing, not shown, and is connected to a heating roller driving motor 16 by a timing belt 15 so as to be rotated by the motor 16. The heating roller driving motor 16 is a stepping motor variable in the rotating direction and the rotating speed. A sensor 14a detects whether or not the heating roller 14 is rotating. When the power source is turned ON, the heating roller 14 should be rotated, but if the heating roller does not rotate, preventive measures against heat are taken as described later, and. for this reason, the sensor 14a detects whether or not the heating roller 14 is rotating.

Reference numeral 17 denotes an electric heater to heat the heating roller 14, and the electric heater 17 produces a quantity of heat to keep the surface temperature of the heating roller 14 at the sterilizing temperature or higher. For convenience of depiction, the electric heater 17 is drawn separately from the heating roller 14, but in actuality, the electric heater 17 is mounted close to the shaft of the heating roller. A switch 18 for controlling the supply of electric power is attached to the line for supplying the heater with electric power, so that the electric heater 17 can be turned ON and OFF by the controller 19. A thermal protector 18a serves as a fuse when the electric heater 17 cannot be turned OFF owing to a fault of the switch 18 even though the electric heater 17 is raised to a specified temperature or higher.

Reference numeral 20 denotes a temperature detector to measure the surface temperature of the heating roller 14, and the measured temperature is input to the controller 19. The controller 19, according to temperature data supplied by the temperature detector 20, controls the switch 18 to manage the surface temperature of the heating roller 14.

Reference numeral 21 denotes a heat-resistant belt, which wraps around the heating roller 14. The belt is under a necessary tension for sterilizing the bills, that is, a tension of 16 kgf or over. The section 22 where the heat-resistant belt 21 and the heating roller 14 are in contact with each other is the bill heating section. The bill heating section 22 is formed by arranging the heat-resistant belt 21 so as to feed bills by pressing the bill against the heating roller 14 for a certain angle or more . As the heating roller 14 and the heat-resistant belt 21 are rotated, the bills which have entered the heating section 22 are heat-sterilized while they are transferred.

Reference numerals 23, 24 denote exhaust and suction fans for preventing the ambient temperature of the sterilizing/disinfecting unit 11 from rising as it is heated by the heating roller 14.

Reference numerals 25, 26 denote respectively, a lock and a lock stopper for the heat-resistant belt 21 which are driven by a solenoid 27 and a gear motor 28, respectively. A sensor 25a senses if the lock 25 is open or closed. The lock 25 in the state shown in FIG. 2 is not covering the sensor 25a, so that the sensor 25a is sensing that the lock 25 is closed. A sensor 26b senses if the lock 26 is open or closed. The lock 26 in the state shown in FIG. 2 is not covering the sensor 26b, so that the sensor 26b is sensing that the lock 26 is closed. Reference numeral 29 denotes a fan to cool the heating roller 14 in an emergency.

In this embodiment, the time for heating a bill at the heating section 22 is 0.05 s and the required sterilizing temperature in this period of time is 160° C. to 240° C.

The surface temperature of the heating roller 14 and the heat-resistant belt 21 is raised by the electric heater 17 for sterilization, and the temperature necessary for sterilization is kept between 160° C. and 240° C., for example, by ON/OFF control of the heater 17.

In the bill sterilizing process, as bills pass through the heating section, the heat of the heating roller 14 and the heat-resistant belt 21 is taken away by the bills, and therefore their surface temperature decreases. To counteract this, some measures should be taken to ensure that the surface temperature of the heating roller 14 and the heat-resistant belt 21 does not fall below the lower limit of sterilizing temperature of 160° C., for example, even after all of the limit number of bills have passed continuously, if only the surface temperature of the heating roller 14 when the first bill passes through the sterilizing section has reached somewhere about 240° C., for example, even though the limit number of bills (100, for example) received or paid in one transaction have moved continuously. If the capacity of the electric heater 17 is increased, the number of bills that can be sterilized continuously will increase, indeed. However, to prevent the surface temperature of the heating roller 14 and the heat-resistant belt 21 from falling below the lower limit of sterilizing temperature when about 2000 continuously transferred bills, for example, are sterilized in loading or recovering bills, a very large electric heater is required, but such a heater will pose problems in terms of power consumption and difficulty in mounting.

With regard to the upper limit of sterilizing temperature, the higher the upper limit, the greater stress will be induced in the heating roller 14, the heat-resistant belt 21 and other materials of the sterilizing section. So, the upper limit of sterilizing temperature is set to be 240° C. obtainable by adding a minimum necessary temperature difference of 80° C., for example, for continuous sterilization, to the sterilization temperature lower limit of 160° C., for example, when the heating time is 0.05 s. The heat-resistant belt is under tension of 16 kgf or more necessary for bill sterilization.

A bill sterilizing process will be described briefly with reference to FIG. 4.

Since it takes time to heat the heating roller 14 and the heat-resistant belt 21 of the bill sterilizing section from room temperature to a specified sterilizing temperature, it is necessary to heat them somewhat in advance. After the power source to the cash transaction machine is turned ON (step 32), the electric heater 17 is turned ON (step 33) to set the heating roller 14 and the heat-resistant belt 21 to a temperature lower than the specified sterilizing temperature, in other words, to about 100° C., for example. The heating roller 14 and the heat-resistant belt 21 are in the standby state until they are heated to a preheating temperature (step 35). When the preheating temperature is reached, preheating temperature holding control is started to keep the surface temperature of the heating roller 14 and the heat-resistant belt 21 at a fixed temperature by turning the electric heater ON and OFF at somewhere about the preheating temperature (step 36). If the heat-resistant belt 21 is kept stationary during the above-mentioned standby state for preheating, there is a possibility that heat is applied only to a part of the heat-resistant belt 21 and that part is damaged. Therefore, it is desirable that the heating roller 14 and the heat-resistant belt 21 should be kept rotating at all times when they are on stand-by. To this end, after the electric heater is turned ON (step 33), the heating roller 14 and the heat-resistant belt 21 are kept rotating at low speed (step 34). At this point in time, the heating roller 14 is rotated only to prevent the heat-resistant belt 21 from being damaged, so that the heating roller 14 has only to be driven at lower speed than normally. While the heating roller 14 and the heat-resistant belt 21 are rotating, it is necessary to make sure that they are rotating without fail. If they are not rotating, this should be regarded as abnormal, and the electric heater 17 needs to be turned OFF to prevent damage to the heat-resistant belt 21 in out-of-step condition. While this preheating temperature holding control is being implemented, the transport paths outside the heating roller 14 and the heat-resistant belt 21 are at a standstill.

The sterilizing section waits under this condition for a transaction involving bill sterilization to start (step 37). When a transaction involving bill sterilization, say, a money paying transaction is selected, the heating roller 14 and the heat-resistant belt 21 are heated to a sterilizing temperature, and the driving speed of the heating roller 14 is accelerated to a bill-transferable speed to implement sterilizing transfer control for sterilizing the bills (step 38). When the sterilizing transfer control (step 38) is finished, the preheating temperature holding control is started again to decrease the surface temperature of the heating roller 14 and the heat-resistant belt 21 and keep them at the preheating temperature (step 39), and the machine waits for a transaction involving bill sterilization to start (step 37). If a transaction without bill sterilization is selected, the heating roller 14 and the heat-resistant belt 21 are rotated at low speed and the surface temperature is at the preheating temperature.

Figure 5:
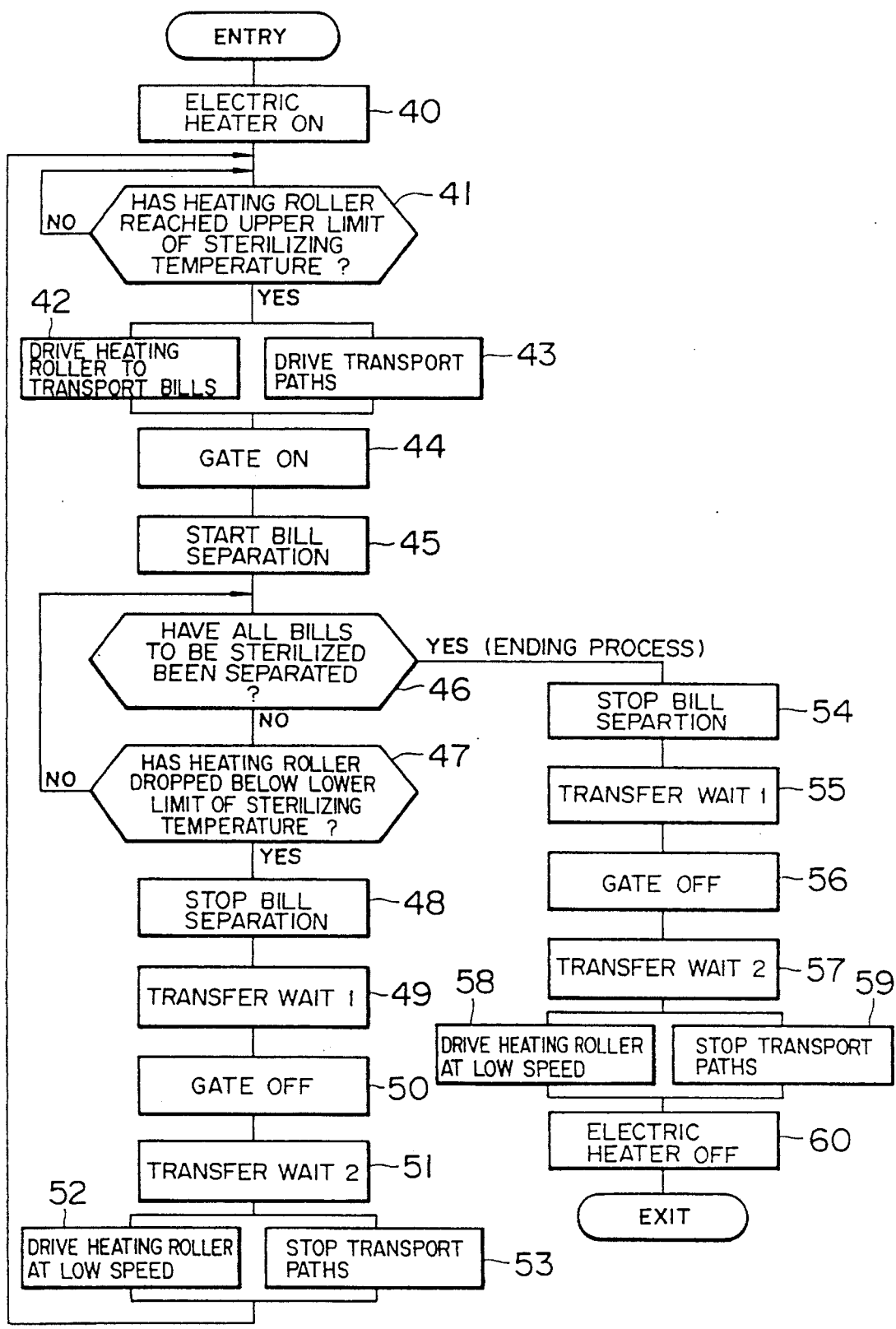
FIG. 5 is a detailed flowchart of sterilizing transport control.

Details of the above-mentioned sterilizing transfer control (step 38) will be described with reference to the flowchart in FIG. 5.

When a transaction involving bill sterilization is selected, in order that the heating roller 14 and the heat-resistant belt 21 which have been held at the preheating temperature should be raised to the sterilizing temperature, the electric heater 17 is turned ON (step 40), and the machine waits for the heating roller 14 and the heat-resistant belt 21 to reach the upper limit of sterilizing temperature (step 41). When they reach the upper limit of sterilizing temperature, the heating roller 14 and the heat- resistant belt 21 are in the state capable of sterilizing the bills. Therefore, the rotating speed of the heating roller 14 is increased to assume the bill-transferable state (step 42). At the same time, the bill transport paths 2, 4, 6, and 7 shown in FIG. 1 are driven (step 43). At this time, the heating roller 14 and the heat-resistant belt 21 are already at the upper limit of sterilizing temperature. An apparently rightful way of thinking would be that the electric heater 17 should be turned OFF, and when the heating roller 14 and the heat-resistant belt 21 fall to the lower limit of sterilizing temperature, the electric heater 17 should be turned ON. However, it is probable that when the bills are passed through the sterilizing section, the heating roller 14 and the heat-resistant belt 21 are deprived of a large quantity of heat by the passing bills, and their temperature may fall considerably. For this reason, the electric heater 17 is left in the ON condition. Some arrangement should be made so that the electric heater 17 is turned OFF if the upper limit of sterilizing temperature is exceeded. Under this condition, the gate 10 is turned ON (step 44), and a separating mechanism, not shown, of the denomination box 8 or 9 is driven to separate the bills (step 45). The bills which have been separated from one another by the separating mechanism are sent onto the transport path 2 one after another at fixed intervals by transfer-means 70 and 71, and are transferred to the bill sterilizing unit 11. The bills transferred on the transport path 2 are switched to the sterilizing route by the gate 10 provided on the transport path 2, and are sent to the sterilizing unit 11. The bills are sent or transferred by the transport path 30 of the sterilizing unit 11 into the heating section 22 between the heating roller 14 and the heat-resistant belt 21. The bills which are held between the heating roller 14 heated to a temperature of 160° C. to 240° C., for example, and the heat-resistant belt 21 are heated and moved through the heating section 22 by the rotation of the heating roller 14 and the heat-resistant belt 21, and sent onto the transport path 31, brought back to the transport path 2 by transport path 31, passed through the discriminator 3, transferred on the transport paths 4, 7, put into the receptacle 1, and drawn out by the user.

By the above operations, the bills are separated and sterilized one after another, and when a specified number of bills have been separated, the ending process is performed (step 46), and for this while, the temperature of the heating roller is monitored to see if it decreases below the lower limit of sterilizing temperature (step 47). In case the selected transaction is a money paying transaction of 100 bills or less, the heating roller does not fall below the lower limit of sterilizing temperature, so that the process proceeds from step 46 to the ending process, the separating operation is stopped (step 54), and the machine waits for the finally separated bill to arrive at the sterilizing unit (step 55), and when the bill arrives, turns the gate 10 OFF (step 56). The machine waits for the last bill to pass the sterilizing unit and arrive at the receptacle 1 shown in FIG. 1 (step 57), and when the last bill arrives, stops the transport paths 2, 4, 6 and 7 (step 59). Moreover, the heating roller 14 is switched to the low-speed drive (step 58), the electric heater 17 is turned OFF (step 60), thereby reducing the temperature of the heating 10 roller 14 and the heat-resistant belt 21. After the above operations are finished, the preheating temperature holding control shown in the flowchart in FIG. 4 is started (step 39), with which the transaction is finished.

In the money paying transaction, the sterilizing unit operates such that the temperature of the heating roller 14 and the heat-resistant belt 21 does not decrease below the lower limit of sterilizing temperature. However, in a recovery transaction or the like, when more than a certain number of bills are passed continuously through the sterilizing section between the heating roller 14 and the heat-resistant belt 21, the sterilizing section sometimes goes down below the lower limit of sterilizing temperature. Therefore, when at step 47 the heating roller goes down below the lower limit of sterilizing temperature during the sterilizing process, the separating operation by the separator is stopped temporarily (step 48), and the machine waits for the finally separated bill to arrive at the sterilizing unit (step 49), and when the bill arrives, turns the gate 10 OFF (step 50), and waits for the final bill to pass through the sterilizing unit and to be stored in the cassette 12 (step 51), and when the bill is stored, stops the transport paths 2, 4, 6 and 7 (step 53). At the same time, the heating roller 14 is switched to the low-speed drive (step 52), and the bill sterilizing process is terminated. Under this condition, the electric heater 17 stays ON, the machine waits for the heating roller 14 and the heat-resistant belt 21 to be restored to the upper limit of sterilizing temperature (step 41), and when the upper limit is reached, the bill sterilizing process is started. When the sterilizing process has been done for all bills, the process moves from step 46 to the ending process. If there are a large number of bills to be sterilized, the above process is repeated.

In the above process, the separating operation is completely stopped. However, the temperature decrease of the heating roller 14 and the heat-resistant belt 21 can be prevented effectively by reducing the number of bills per unit time to be sent in between the heating roller 14 and the heat-resistant belt 21 by decreasing the separating speed, or not only by this decreasing the separating speed but also by decreasing the transfer speed of the transport path 2 and the rotating speed of the heating roller 14.

Figure 4:
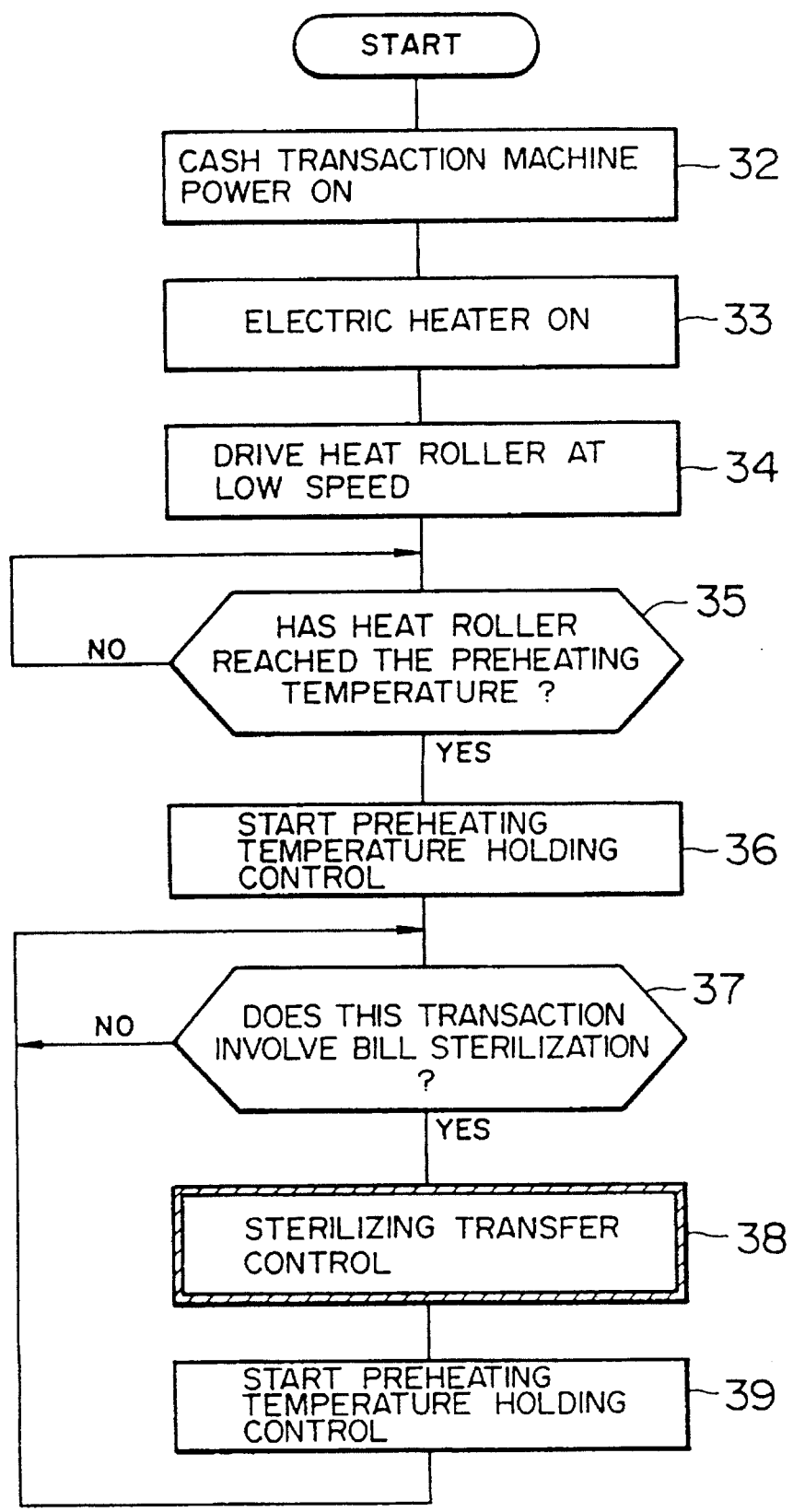
FIG. 4 is a flowchart of operation control in sterilizing bills.

In the case of another embodiment shown in FIG. 6, the "received money counting process in a money receiving transaction" at step 37 in FIG. 4 is performed as the "transaction involving bill sterilization" by the same control described above.

Figure 7:
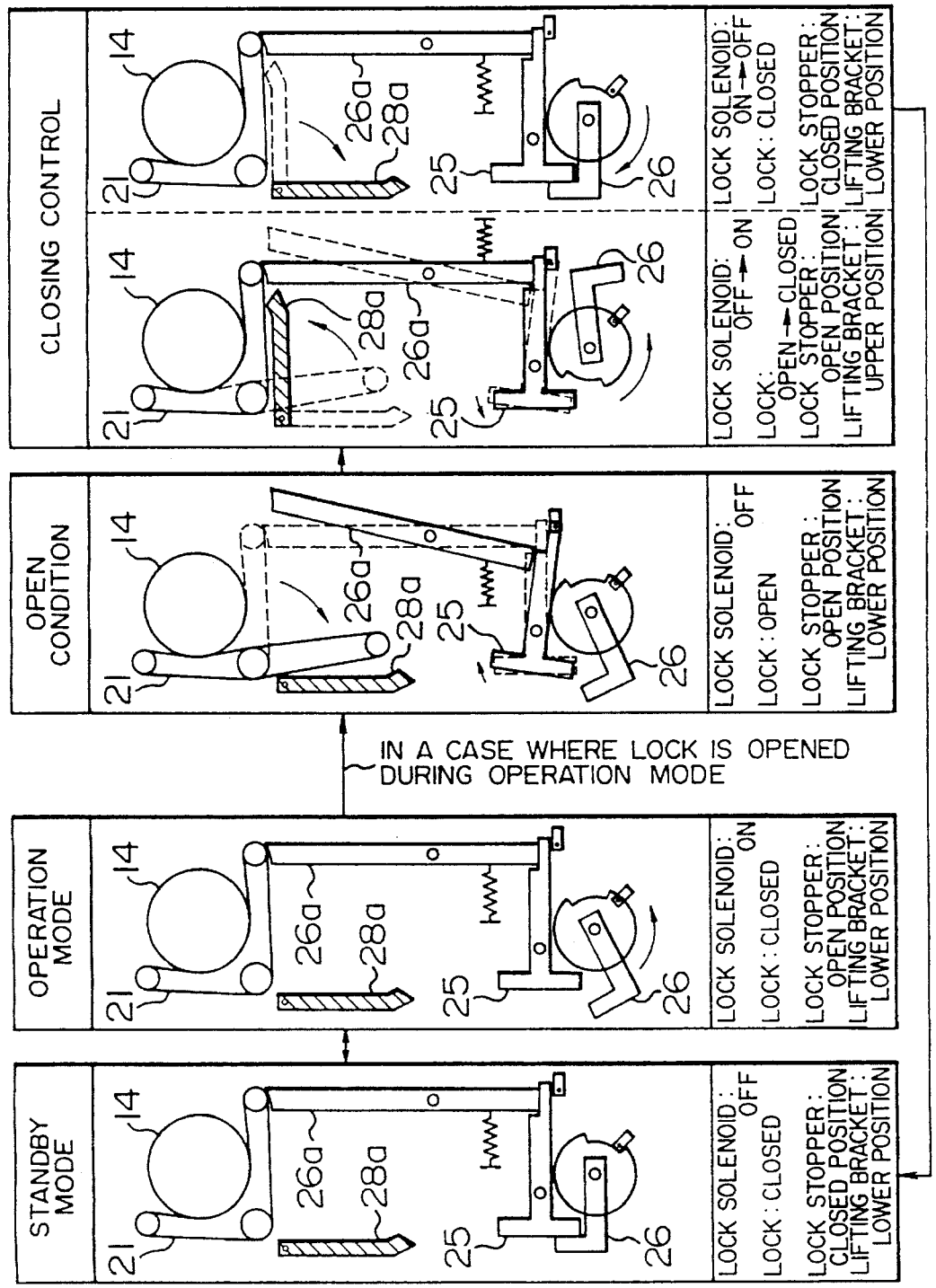
FIG. 7 is a diagram showing opening/closing control of the heat-resistant belt.

With reference to FIG. 2, description will now be made of a process to be executed when abnormality occurs in the sterilizing section during the sterilizing process. When bills are left untransported in the heating section 22, if the bills are in contact with the heating roller 14 for a long time, the bills may be damaged. When the bills are left untransported, the power source to the lock solenoid 27 is turned OFF, the lock 25 is released, causing the heat-resistant belt 21 to be disengaged, so that the bills stuck in the heating section 22 are released. When the lock 25 of the heat-resistant belt 21 is released, the fan 29 installed above the heating roller 14 is rotated to quickly cool the heating roller 14 as an emergency step. Another effect of rotating the fan 29 is to blow off the bills left untransported in and around heating section 22. The heat-resistant belt 21, which in the open state, is so designed as to be restored to the initial state by being automatically placed in the locked condition. Details of opening/closing control of the heat-resistant belt 21 will be described with reference to FIG. 7.

The lock mechanism is normally in the standby mode, the lock 25 is fixed by the lock stopper 26, and the lock lever 26a used to support the heat-resistant belt 21 is held by the lock 25 while the lock lever 26a is in a condition supporting the heat-resistant belt 21. (standby mode)

When a money paying transaction is started, the lock solenoid 27 is turned ON to hold the lock 25, and at the same time, the lock stopper 26 is moved to the open position by the stopper motor 28 in FIG. 2. As a result, the lock 25 is placed in the closed or open condition according to ON/OFF condition of the lock solenoid 27. (operation mode)

Under this condition, when abnormality occurs, the lock solenoid 27 is turned OFF, thus placing the lock 25 in the open condition. Accordingly, the lock lever 26a is disengaged, and the heat-resistant belt 21 is opened. (open condition)

Under this condition, the heating roller 14 and the heat-resistant belt 21 continue to rotate for a specified amount and stop after all bills sent by the gate 10 into the sterilizing section are released.

The closing process takes place as follows. When the transport paths are stopped, the remaining bills are removed, and then the heat-resistant belt 21 is closed. (closing process)

When the lock stopper motor 28 is rotated for a specified amount, a lifting bracket 28a turns to move the heat-resistant belt 21 to the closed position, and the lock lever 26a moves to a position where the lock lever supports the heat-resistant belt 21. Under this condition, the lock solenoid 27 is turned ON, so that the lock 25 locks the lock lever 26a. Under this condition, the stopper motor 28 is rotated in reverse direction, thus placing the lock stopper in the closed position to fix the lock 25. Even if under this condition the lock solenoid 27 is turned OFF, the lock 25 is supported by the lock stopper 26. Thus, the lock mechanism is in the standby mode. (standby mode)

Figure 8:
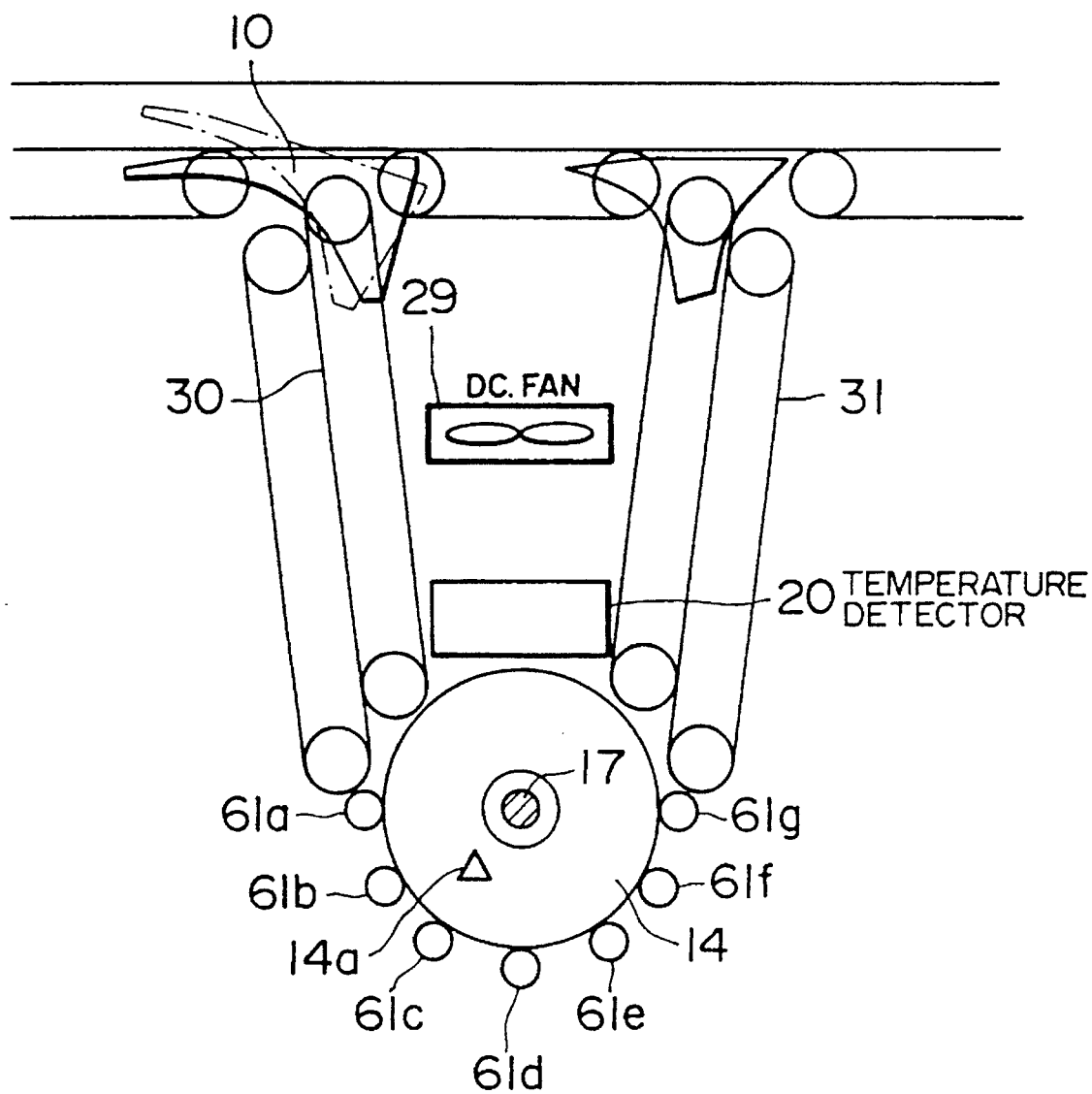
FIG. 8 is a diagram showing an illustrative embodiment of the heat sterilizing section.

In the above description, the sterilizing/ disinfecting unit for sterilizing the bills is formed by the heating roller 14 and a heat-resistant belt 21 disposed as if to surround the heating roller 14, as shown in FIG. 2. If the sterilizing/disinfecting unit is formed by the heating roller 14 and a plurality of rollers 61a to 61g placed against the circumference of the heating roller 14 as shown in FIG. 8, the bills passing through the heating section 22 sufficiently wrap around the heating roller 14 and are thereby heated. Therefore, it is expected that the same effects can be obtained as in the sterilizing/disinfecting unit formed by the heating roller 14 and the heat-resistant belt 21. In other words, the bills are transported while they are pressed against the heating roller 14 for more than a certain angle or more.

Another embodiment of the present invention will next be described.

There are many germs adhering to the bills. In this embodiment, the kinds of germs to be killed are limited, and for this purpose, effective sterilizing conditions are set. Among the germs adhering to the bills, *staphylococcus aureus* causes food poisoning and is also drawing attention as a germ causing hospital infection, and therefore must be a target of sterilization. The germs with high pathogenicity, such as a coliform bacillus, which could be a direct cause of food poisoning, are equal to or weaker than *staphylococcus aureus* in resistance to heat. If sterilizing efforts are directed to *staphylococcus aureus*, the other germs can be killed. Bacillus subtilis is a germ having a character like an enzyme and is generally harmless, so that if the germ is excluded from the targets of sterilization, this will not pose any problem. For the reasons mentioned above, the targets of sterilization include *staphylococcus aureus* and other germs low in resistance to heat. With regard to the germicidal effect to the germs as the targets of sterilization, to reduce the germs to about one-tenth, in other words, the germicidal rate of about 90% is considered effective because this machine is used in everyday life and the germs to be killed adhere to the users' skin. According to the earlier-mentioned "Principal Sterilization and Disinfection in Practice - revised edition -", the heating time for killing 90% (reducing the number of germs to $\frac{1}{10}$) by the sterilizing process is referred to as the D value (Decimal reduction value), and this is used as a common concept in sterilization.

Figure 9:
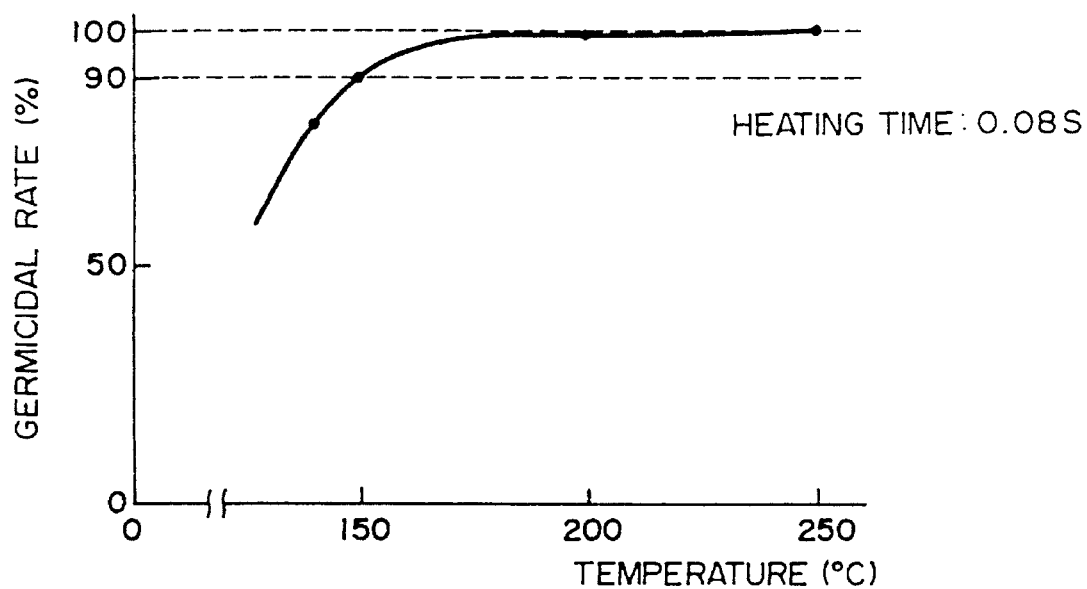
FIG. 9 is a diagram showing the relation between the heating temperature and the death rate for *staphylococcus aureus*.
Figure 10:
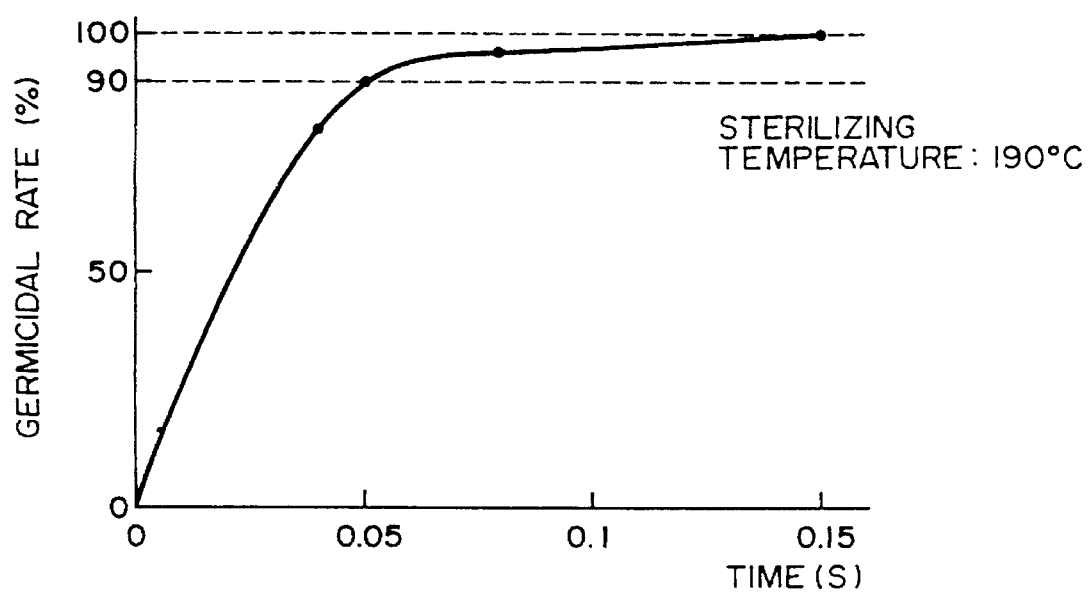
FIG. 10 is a diagram showing the relation between the heating time and the death rate for *staphylococcus aureus*.
Figure 11:
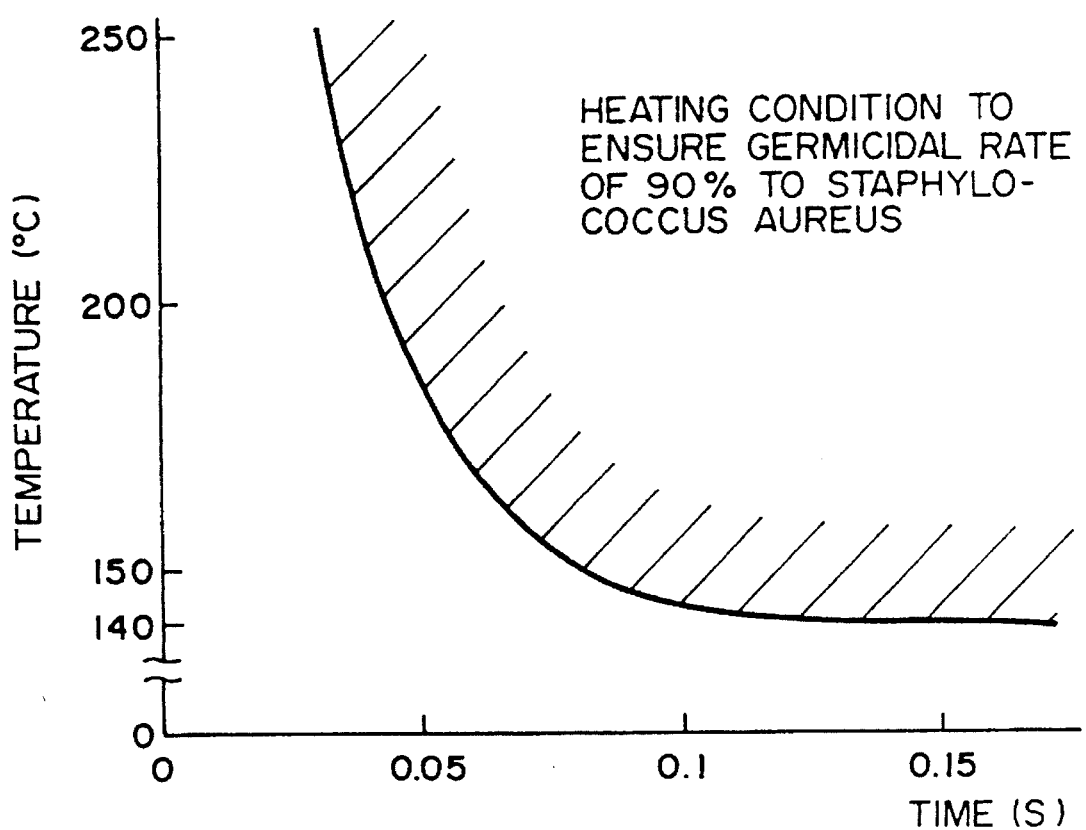
FIG. 11 is a diagram showing the germicidal effect by the relation between the heating time and the heating temperature for *staphylococcus aureus*.

The present inventors obtained experimental results as follows. The experimental results, shown in FIGS. 9 to 11, are the relations between the germicidal effects, and the heating time and heating temperature in the case of *staphylococcus aureus* when the bill sterilizing or disinfecting means comprises a rotating heating roller capable of heating the bills and a belt which, while being pressed against the heating roller, rotates in wrap-around contact with the heating roller. FIG. 9 shows the relation between the heating temperature and the germicidal rate when the heating time is 0.08 s and indicates that 90% of the germs can be killed at about 150° C. FIG. 10 shows the relation between the heating time and the germicidal rate when the heating temperature is 190° C. and indicates that 90% of the germs can be killed when the heating time is 0.05 s. FIG. 11 shows the heating condition which should satisfy the target value of 90% of the germicidal rate based on the experimental results using the heating time and temperature as parameters. From this, it has been clarified that to achieve about 90% of the germicidal rate to *staphylococcus aureus* as the target of sterilization when the heating time is about 0.15 s, the heating temperature needs to be about 140° C. or above, and that in order to achieve about 90% of the germicidal rate when the heating time is 0.05 s, the heating temperature need to be about 185° C. or above.

Therefore, in a cash transaction machine, *staphylococcus aureus* and other germs weaker in resistance to heat than *staphylococcus aureus* are set as the targets of sterilization, the diameter and the rotating speed of the heating roller are set arbitrarily by controlling the heating roller surface temperature so as to be 140° C. or in a specified temperature range of 140° C. or above and by controlling the time of a bill being held between the heating roller and the heat-resistant belt wrapping around the heating roller so as to be in a range from 0.05 s or over to 0.15 s or less.

By dry air sterilization for heat-sterilizing the bills by the heating roller as mentioned above, the bills, while they are transferred, are heated to the heating temperature of 140° C. or above for a time corresponding to the D value of 0.05 to 0.15 s. The D value for reducing the germs to 1/10 can be made a value which is applicable to an ordinary cash transaction machine and suitable for the processing time and the transfer speed of an ordinary cash transaction machine, and can be secured without prolonging the processing time.

An embodiment which uses the above-mentioned condition will now be described. In this embodiment, the cash transaction machine is of the construction shown in FIG. 6, and the bill sterilizing unit 11 shown in FIG. 2 is used.

The heating roller 14 is an aluminum roller 60 mm in diameter, and its temperature is controlled so as to be about 185° to 190° C. at all times by the controller 19 according to information from the temperature detector 20. The heating roller 14 rotates at a speed of 6.5 revolutions/s. This heating roller speed is set so that the transfer speed of 1.2 m/s of the transfer mechanisms 2, 4 and 7 substantially coincides with the peripheral speed of the heating roller 14. The heat-resistant belt 21 wraps for about 180 degrees around the periphery of the heating roller 14, so that the bills transferred between the heating roller 14 and the heat-resistant belt 21 contact the heating roller 14 for about 0.08 s. In the above-mentioned embodiment, preheating temperature holding control at 100° C. is performed, but in this embodiment, the heating roller 14 and the heat-resistant belt 21 are controlled so as to be 180° to 190° C. at all times to be ready for a quick start of the sterilizing process.

Moreover, the machine in this case handles a maximum of 100 bills collectively, and processes the bills at a speed of 8 bills a second. The sterilizing/ disinfecting unit 11 handles the bills at the same speed. In this process, if the quantity of received heat in the bills is greater than the quantity of heat supplied by the electric heater 17, the temperature of the heating roller 14 does not fall. In this embodiment, however, because of the restriction on the maximum power consumption, the temperature of the heating roller 14 was measured and found to be decreasing gradually, and after a continuous processing of a maximum of 100 bills, the heating roller 14 was found to have a temperature of about 150° C. by measurement. Therefore, when a maximum of 100 bills are processed continuously, the heating condition on the last bill for killing 90% of *staphylococcus aureus* as described with reference to FIG. 11 is satisfied sufficiently, and therefore the appropriate sterilizing effects can be obtained.

In order to increase the number of bills to be sterilized continuously to more than 100 in this embodiment, it is only necessary to further raise the initial setting temperature of the heating roller 14. However, because the heat resistance of the rubber or resin parts needs to be increased, and also for reasons of technology and price, about 250° C. is considered to be the limit.

Figure 12A:
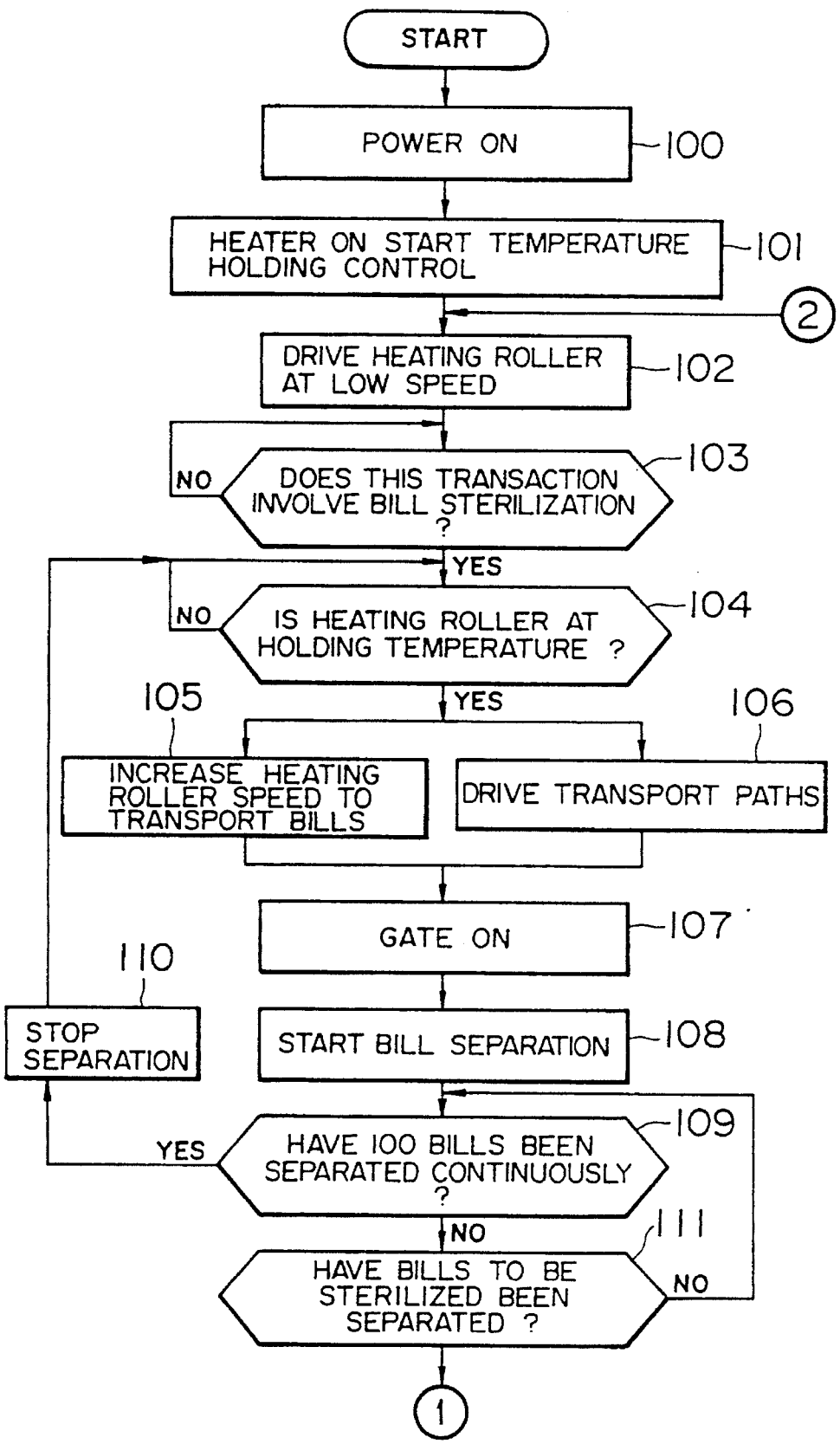
FIGS. 12A and 12B are flowcharts of operation control in the other embodiment of the present invention.
Figure 12B:
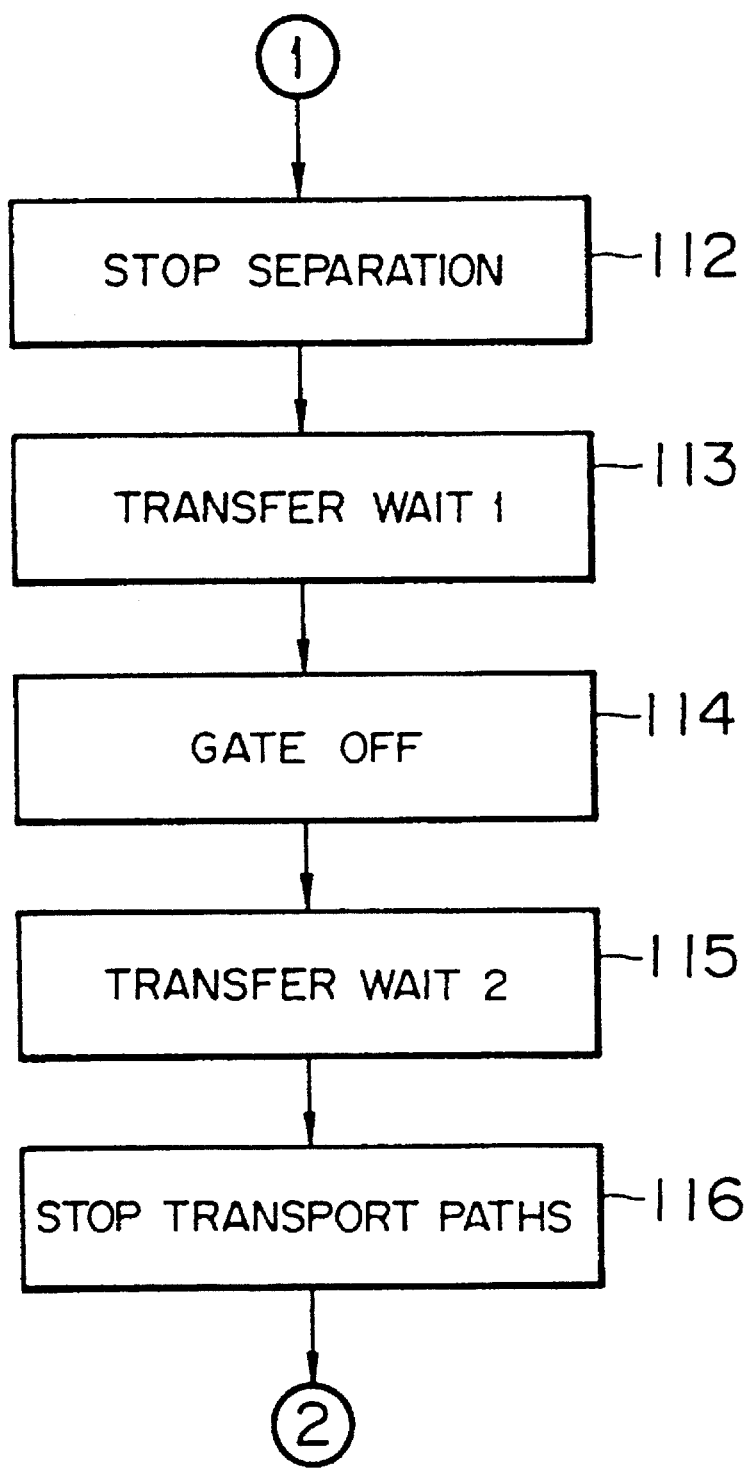

FIGS. 12A and 12B are flowcharts of operation control.

After power is applied to the cash transaction machine (step 100), the electric heater 17 is turned ON, and temperature holding control is started to hold the heating roller 14 and the heat-resistant belt 21 in a range of 185° to 190° C. (step 101). The heating roller 14 and the heat-resistant belt 21 are driven at low speed (step 102). The transport paths other than the heating roller 14 and the heat-resistant belt 21 are kept stationary.

The sterilizing unit is at the standby, waiting for a transaction involving bill sterilization to start (step 103). When a transaction involving bill sterilization, that is, a money receiving transaction, for example, is selected, a decision is made whether or not the heating roller 14 is at a holding temperature 185° to 190° C. (step 104). When the heating roller 14 is at the holding temperature of 185° to 190° C., the sterilizing unit is ready for the sterilization process, the rotating speed of the heating roller 14 is increased to make it possible to transport bills (step 105), and at the same time the bill transport paths 2, 4, 6 and 7 shown in FIG. 6 are driven (step 106). Under this condition, the gate 10 is turned ON (step 107), a separating mechanism, not shown, of the temporary accumulation mechanism 5 is driven to start the separation of bills (step 108). The bills separated by the separating mechanism are sent onto the transport path 6 one by one spaced at fixed intervals, and the bills are transferred through the discriminator 3, the transport paths 4, 7 and 2 to the bill sterilizing unit 11. The bills are sent through the transport path 2 switched to the sterilizing route by the gate 10 provided on the transport path 2, and sent to the sterilizing unit 11. The bills are transferred on the transport path 30 of the sterilizing unit 11 into the heating section 22 between the heating roller 14 and the heat-resistant belt 21. The bills, which are placed between the heating roller 14 and the heat-resistant belt 21, are moved through the heating section 22 by the rotation of the heating roller 14 and the heat-resistant belt 21, and transferred onto the transport path 31, brought back to the transport path 2, and finally stored in the denomination box 8 or 9.

Since, by the above operations, the bills are separated and sterilized one after another, a decision is made whether or not 100 bills have been separated continuously (step 109). If 100 bills have been separated continuously, the separating operation is stopped 10 temporarily (step 110), and the temperature of the heating roller 14 is brought to 185° to 190° C. When all bills have been separated (step 111), the separating operation is stopped (step 112), the machine waits for the finally separated bill to arrive at the sterilizing unit (step 113), turns the gate 10 OFF (step 114), and waits for the last bill to pass through the sterilizing unit and to be stored in the denomination box (step 115), then stops the transport paths 2, 4, 6 and 7 (step 116).

The temperature range of 185° to 190° C. as the heating temperature condition adopted in this embodiment is about the same level as the heating temperature condition of the thermal fixing unit in a copier or laser beam printer of late. Therefore, if parts, such as a safety device against heat or fire, which have proven performance in terms of heat resistance, can be diverted to the cash transaction machine, this will greatly contribute to the improvement of reliability and the reduction of price of the machine.

In this embodiment, *staphylococcus aureus* and the germs with weaker resistance to heat are set as the targets of sterilization, and the diameter and the rotating speed of the heating roller are set so that the time of a bill being placed between the heating roller and the heat-resistant belt wrapping around the heating roller may be 0.08 s. By controlling the surface temperature of the heating roller so as to be in a range of 185° to 190° C., the germicidal rate of about 90% can be secured for a continuous processing of 100 bills transferred at a speed of 8 bills a second. Even after a continuous sterilizing process is performed, if the output of the electric heater is increased to prevent the surface temperature of the heating roller from falling, sufficient sterilizing effects can be obtained with the heating roller whose surface temperature is about 150° C.

When the diameter of the heating roller 14 is smaller than 60 mm in this embodiment, or when the transfer speed is faster than 1.2 m/s in this embodiment, or when the wrapping angle of the heat-resistant belt 21 around the periphery of the heating roller 14 is smaller than about 180 degrees in this embodiment, the heating time can be shorter than 0.08 s in this embodiment. When a machine has a heating time of 0.05 s, for example, if the surface temperature of the heating roller is set to be 215° to 220° C., for example, the same sterilizing effects as in the aforementioned embodiment can be obtained.

In this embodiment, the germs to be killed are *staphylococcus aureus* and other germs weaker in heat resistance than *staphylococcus aureus*, but if bacillus subtilis with higher heat resistance than *staphylococcus aureus* is included in the targets of sterilization, necessary and sufficient heating conditions can be set by examining the sterilizing effects by experiment like in the cases mentioned above.

We claim:

1. A cash transaction machine for performing receiving transactions and/or paying transactions of bills by a user's manipulation, comprising:

a receptacle for depositing and withdrawing said bills;

a first storage means for storing said bills;

transport means for transferring said bills between said receptacle and said first storage means, said transport means including transport paths for said bills;

heating means for heating said bills; and transfer means for transferring said bills between one of said transport paths and said heating means, wherein said heating means and said first storage means are arranged in said cash transaction machine such that said storing of said bills and said heating of said bills take place in respective positions along one side of one of said transport paths.

2. A cash transaction machine according to claim 1, wherein said heating means and said first storage means are arranged in said machine below said one side of said one of said transport paths.

3. A cash transaction machine according to claim 2, wherein said one side of said one of said transport paths is formed substantially straight and wherein said heating means and said first storage means are arranged in a line along and below said one side of said one of said transport paths.

4. A cash transaction machine according to claim 3, further comprising at least a second storage means for storing said bills, wherein said second storage means, said first storage means and said heating means are arranged in a line along and below said one side of said one of said transport paths, and said heating means is arranged at an end of said line.

5. A cash transaction machine according to claim 4, wherein said cash transaction machine includes an outer wall, and wherein said heating means arranged at said end of said line is closer than said first and second storage means to said outer wall of said cash transaction machine.

6. A cash transaction machine according to claim 4, further comprising discriminating means for discriminating said bills, said discriminating means being arranged in said cash transaction machine along a second side of said one of said transport paths above said one side thereof, and wherein said heating means is arranged at a position more distant than said first and second storage means from said discriminating means.

7. A cash transaction machine according to claim 6, wherein said receptacle is arranged in said cash transaction machine above said one of said transport paths.

8. A cash transaction machine according to claim 1, wherein said heating means includes means for transporting said bills in said heating means as the bills are being heated, first means for heating said bills, second means for pressing said bills upward against said first means, means for releasing said second means from pressing said bills upward against said first means, and control means for ending the state that said bills are held pressed between said first and second means by actuating said releasing means when said bills are left untransported by said means for transporting said bills in said heating means.

9. A cash transaction machine according to claim 8, further comprising means for cooling said heating means by blowing air thereto when said bills are left untransported by said means for transporting said bills in said heating means.

10. A cash transaction machine according to claim 1, further comprising:

temperature detecting means for sensing a temperature of said heating means; and control means for controlling a bill heating temperature of said heating means for heating said bills in a specified temperature range in response to the temperature detected by said detecting means, and controlling transactions according to said temperature.

11. A cash transaction machine according to claim 10, wherein said heating means includes a rotatable heating roller, a rotatable heating transfer means for transferring said bills by pressing said bills against said heating roller for a fixed angle or more of rotation of said heating roller, and heating means for heating said heating roller, and wherein said control means controls said heating roller and said heating transfer means to rotate even when said heating means does not perform.

12. A cash transaction machine according to claim 11, wherein said control means controls said heating roller and heating transfer means so that they rotate at low speed even when said heating means does not perform.

13. A cash transaction machine according to claim 10, wherein said control means limits the number of bills to be heated continuously.

14. A cash transaction machine according to claim 11, wherein said control means includes means for moving said heating transfer means to a position away from said heating roller.

15. A cash transaction machine according to claim 10, wherein said control means controls the heating temperature of said heating means to 140° C. or above.

16. A cash transaction machine for performing receiving transactions and/or paying transactions of bills by a user's manipulation, comprising:
  a receptacle for depositing and withdrawing said bills;
  a first storage means for storing said bills;
  transport means for transferring said bills between said receptacle and said first storage means, said transport means including transport paths for said bills;
  heating means for heating said bills; and
  transfer means for transferring said bills between one or said transport paths and said heating means
  wherein said heating means and said first storage means are arranged in said cash transaction machine in respective positions along one side of one of said transport paths, and wherein said control means controls the heating temperature and time of said heating means to a heating temperature of 140° C. or above and a heating time of 0.05 to 0.15 s.

17. A cash transaction machine for performing receiving transactions and/or paying transactions of bills by a user's manipulation, comprising:
  a receptacle for depositing and withdrawing said bills;
  a first storage means for storing said bills;
  transport means for transferring said bills between said receptacle and said first storage means, said transport means including a transport path for said bills;
  sterilizing means for heat-sterilizing said bills; and
  transfer means for transferring said bills between said transport path and said sterilizing means,
  wherein said sterilizing means and said first storage means are arranged in said cash transaction machine such that said storing of said bills and said heat sterilizing of said bills take place in respective positions along one side of by said transport path.

18. A cash transaction machine according to claim 17, wherein said sterilizing means and said first storage means are arranged in said machine below said one side of said transport path.

19. A cash transaction machine according to claim 18, wherein said one side of said transport path is substantially straight, and wherein said sterilizing means and said first storage means are arranged in a line along and below said one side of said transport path.

20. A cash transaction machine according to claim 19, further comprising at least a second storage means for storing said bills, wherein said second storage means, said first storage means and said sterilizing means are arranged in a line along and below said one side of said transport path, and said sterilizing means is arranged at an end of said line.

21. A cash transaction machine according to claim 20, wherein said cash transaction machine includes an outer wall and wherein said sterilizing means arranged at said end of said line is closer to said outer wall of said cash transaction machine than said first and second storage means.

22. A cash transaction machine according to claim 20, further comprising discriminating means for discriminating said bills, said discriminating means being arranged in said cash transaction machine along a second side of said transport path above said one side of said transport path, and wherein said sterilizing means is arranged at a position more distant than said first and second storage means from said discriminating means.

23. A cash transaction machine according to claim 22, wherein said receptacle is arranged in said cash transaction machine above said transport path.

24. A cash transaction machine according to claim 17, wherein said sterilizing means includes means for transporting said bills in said sterilizing means as they are being heat-sterilized, first means for heating said bills, second means for pressing said bills upward against said first means, means for releasing said second means from pressing said bills upward against said first means, and control means for ending the state that said bills are held pressed between said first and second means by actuating said releasing means when said bills are left untransported by said means for transporting said bills in said sterilizing means.

25. A cash transaction machine for performing receiving transactions and/or paying transactions of bills by a user's manipulation, comprising:
  a receptacle for depositing and withdrawing said bills;
  a first storage means for storing said bills;
  transport means for transferring said bills between said receptacle and said first storage means, said transport means including a transport path for said bills;
  sterilizing means for heat-sterilizing said bills; and
  transfer means for transferring said bills between said transport path and said sterilizing means,
  wherein said sterilizing means and said first storage means are arranged in said cash transaction machine in respective positions along one side of said transport path, and wherein said sterilizing means includes means for transporting said bills in said sterilizing means as they are being heat-sterilized, first means for heating said bills, second means for pressing said bills upward against said first means, means for releasing said second means from pressing said bills upward against said first means, and control means for ending the state that said bills are held pressed between said first and second means by actuating said releasing means when said bills are left untransported by said means for transporting said bills in said sterilizing means, and said machine further comprising means for cooling said sterilizing means by blowing air thereto when said bills are left untransported by said means for transporting said bills in said sterilizing means.

26. A cash transaction machine for performing receiving transactions and/or paying transactions of bills by a user's manipulation, comprising:
  a receptacle for depositing and withdrawing said bills;
  a first storage means for storing said bills;
  transport means for transferring said bills between said receptacle and said first storage means, said transport means including a transport path for said bills;
  sterilizing means for heat-sterilizing said bills; and
  transfer means for transferring said bills between said transport path and said sterilizing means,
  wherein said sterilizing means and said first storage means are arranged in said cash transaction machine in respective positions along one side of said transport path, and said cash transaction machine further comprising means for constantly cooling the surroundings of said sterilizing means.

27. A cash transaction machine for performing receiving transactions and/or paying transactions of bills by a user's manipulation, comprising:
  a receptacle for depositing and withdrawing said bills;
  a first storage means for storing said bills;
  transport means for transferring said bills between said receptacle and said first storage means, said transport means including a transport path for said bills;

sterilizing means for heating-sterilizing said bills; and transfer means for transferring said bills between said transport path and said sterilizing means, wherein said sterilizing means and said first storage means are arranged in said cash transaction machine in respective positions along one side of said transport path, and said cash transaction machine further comprising air moving means constantly causing the air around the said sterilizing means to pass on.

28. A cash transaction machine according to claim 27, wherein said air moving means comprises a fan and said fan is arranged at a bottom face of said cash transaction machine.

29. A cash transaction machine for performing receiving transactions and/or paying transactions of bills by a user's manipulation, comprising:

a receptacle for depositing and withdrawing said bills;

a first storage means for storing said bills;

transport means for transferring said bills between said receptacle and said first storage means, said transport means including a transport path for said bills;

sterilizing means for heat-sterilizing said bills; and transfer means for transferring said bills between said transport path and said sterilizing means, wherein said sterilizing means and said first storage means are arranged in said cash transaction machine in respective positions along one side of said transport path, and said cash transaction machine further comprising means for cooling the bills heated by said sterilizing means.

30. A cash transaction machine according to claim 29, wherein said bill cooling means cools the bills as they are being transported by the transport means.

31. A cash transaction machine for performing receiving transactions and/or paying transactions of bills by a user's manipulation, comprising:

a receptacle for depositing and withdrawing said bills;

a first storage means for storing said bills;

transport means for transferring said bills between said receptacle and said first storage means, said transport means including a transport path for said bills;

disinfecting means for heat-disinfecting said bills; and transfer means for transferring said bills between said transport path and said disinfecting means, wherein said disinfecting means and said first storage means are arranged in said cash transaction machine such that said storing of said bills and said heat-disinfecting of said bills take place in respective positions along one side of said transport path.

32. A cash transaction machine for performing receiving transactions and/or paying transactions of bills by a user's manipulation, comprising:

a receptacle for depositing and withdrawing said bills;

a first storage means for storing said bills, transport means for transferring said bills between said receptacle and said first storage means, said transport means including transport paths for said bills;

heating means for heating said bills; and transfer means for transferring said bills between one of said transport paths and said heating means, wherein said heating means and said first storage means are arranged in said cash transaction machine in respective positions along one side of one of said transport paths, and said cash transaction machine further comprising means for constantly cooling the surroundings of said heating means.

33. A cash transaction machine for performing receiving transactions and/or paying transactions of bills by a user's manipulation, comprising:

a receptacle for depositing and withdrawing said bills;

a first storage means for storing said bills, transport means for transferring said bills between said receptacle and said first storage means, said transport means including transport paths for said bills;

heating means for heating said bills; and transfer means for transferring said bills between one of said transport paths and said heating means, wherein said heating means and said first storage mean are arranged in said cash transaction machine in respective positions along one side of one of said transport paths, and wherein said heating means and said first storage means are arranged in said cash transaction machine below said one side of said one of said transport paths and said cash transaction machine further comprising air moving means constantly causing the air around the said sterilizing means to pass on.

34. A cash transaction machine according to claim 33, wherein said air moving means comprises a fan and said fan is arranged at a bottom face of said cash transaction machine.

35. A cash transaction machine for performing receiving transactions and/or paying transactions of bills by a user's manipulation, comprising:

a receptacle for depositing and withdrawing said bills;

a first storage means for storing said bills, transport means for transferring said bills between said receptacle and said first storage means, said transport means including transport paths for said bills;

heating means for heating said bills; and transfer means for transferring said bills between one of said transport paths and said sterilizing means, wherein said heating means and said first storage means are arranged in said cash transaction machine in respective positions along one side of one of said transport paths, and said cash transaction machine further comprising means for cooling the bills heated by said heating means.

36. A cash transaction machine according to claim 35, wherein said bill cooling means cools the bills as they are being transported by said transport means.

37. A cash transaction machine for performing receiving transactions and/or paying transactions of bills by a user's manipulation, comprising:

a receptacle for depositing and withdrawing said bills;

a denomination box for storing said bills;

a sterilizer for heat-sterilizing said bills; and a transport path along which said bills can be transferred between said receptacle, said denomination box and said sterilizer, said transport path including a substantially horizontal portion, wherein said sterilizer and said denomination box are arranged in said machine such that said storing of said bills and said heat-sterilizing of said bills take place in respective positions below and along said substantially horizontal portion of said transport path.

38. A cash transaction machine for performing receiving transactions and/or paying transactions of bills by a user's manipulation, comprising:

a receptacle for depositing and withdrawing said bills;

a denomination box for storing said bills, said denomination box being accommodated in a space in said machine;

transport equipment for transferring said bills between said receptacle and said denomination box accommodated in said space, said transport equipment transferring said bills along a substantially horizontal path;

a sterilizer for transferring said bills to and from said transport equipment, and heat-sterilizing said bills; and a box for accommodating said sterilizer, wherein said box accommodating said sterilizer and said space accommodating said denomination box are arranged such that said heat-sterilizing of said bills and said storing of said bills take place in respective positions along the underside of said substantially horizontal path.

39. A cash transaction machine according to claim 38, wherein said sterilizer includes means for transporting said bills in said sterilizer, first means for heating said bills, second means for pressing said bills upward against said first means, means for releasing said second means from pressing said bills upward against said first means for heating, and control means for ending the state that said bills are held by said first and second means by actuating said releasing means when said bills are left untransported by said means for transporting said bills in said sterilizer.

40. A cash transaction machine for performing receiving transactions and/or paying transactions of bills by a user's manipulation, comprising:

a receptacle for depositing and withdrawing said bills;

a denomination box for storing said bills, said denomination box being accommodated in a space in said machine;

transport equipment for transferring said bills between said receptacle and said denomination box accommodated in said space, said transport equipment transferring said bills along a substantially horizontal path;

a sterilizer for transferring said bills to and from said transport equipment, and heat-sterilizing said bills; and a box for accommodating said sterilizer, wherein said box accommodating said sterilizer and said space accommodating said denomination box are arranged in respective positions along the underside of said substantially horizontal path, wherein said sterilizer includes means for transporting said bills in said sterilizer, first means for heating said bills, second means for pressing said bills upward against said first means, means for releasing said second means from pressing said bills upward against said first means for heating, and control means for ending the state that said bills are held by said first and second means by actuating said releasing means when said bills are left untransported by said means for transporting said bills in said sterilizer, and wherein said box comprises means for cooling said sterilizer by blowing air thereto when said bills are left untransported.

41. A cash transaction machine according to claim 40, wherein said cooling means comprises a fan arranged above said sterilizer, said fan blowing air strong enough to separate said bills from said sterilizer.

42. A cash transaction machine for performing receiving transactions and/or paying transactions of bills by a user's manipulation, comprising:

a receptacle for depositing and withdrawing said bills;

a denomination box for storing said bills, said denomination box being accommodated in a space in said machine;

transport equipment for transferring said bills between said receptacle and said denomination box accommodated in said space, said transport equipment transferring said bills along a substantially horizontal path;

a sterilizer for transferring said bills to and from said transport equipment, and heat-sterilizing said bills; and a box for accommodating said sterilizer, wherein said box accommodating said sterilizer and said space accommodating said denomination box are arranged in respective positions along the underside of said substantially horizontal path, wherein an air hole is opened in a bottom face of said box, and wherein said cash transaction machine has a fan, provided at a position corresponding to said air hole, to discharge the air from said box through said air hole.

43. A cash transaction machine comprising:

a bill transport path; and a bill sterilizing unit mounted within said cash transaction machine and including a sterilizing means for heat-sterilizing bills, means for transferring bills between said bill transport path of said cash transaction machine and said sterilizing means, a box located within said cash transaction machine and covering said sterilizing means and said transfer means, and air moving means constantly causing the air around said sterilizing means within said box to move on, said air moving means including an air hole opened in a bottom face of said box, said air hole being located opposite to an exhaust fan arranged outside said box at a bottom portion of said cash transaction machine.

44. A cash transaction machine for performing receiving transactions and/or paying transactions of bills by a user's manipulation, comprising:

a receptacle for depositing and withdrawing said bills;

a first storage means for storing said bills;

transport means for transferring said bills between said receptacle and said first storage means, said transport means including a transport path for said bills;

sterilizing means for heat-sterilizing said bills; and transfer means for transferring said bills between said transport path and said sterilizing means, wherein said sterilizing means and said first storage means are arranged in said cash transaction machine in respective positions along one side of said transport path, and wherein said sterilizing means includes means for transferring said bills, which are transferred by said transfer means to said sterilizing means, back to said transfer means after heat-sterilizing of said bills and without a stop.

45. A cash transaction machine for performing receiving transactions and/or paying transactions of bills by a user's manipulation, comprising:

a receptacle for depositing and withdrawing said bills;

a first storage means for storing said bills;

transport means for transferring said bills between said receptacle and said first storage means, said transport means including transport paths for said bills;

heating means for heating said bills; and transfer means for transferring said bills between one of said transport paths and said sterilizing means, wherein said heating means and said first storage means are arranged in said cash transaction machine in respective positions along one side of one of said transport paths, and wherein said heating means includes means for transferring said bills, which are transferred by said transfer means to said heating means, back to said transfer means after heating of said bills and without a stop.

46. A cash transaction machine for performing receiving transactions and/or paying transactions of bills by a user's manipulation, comprising:

a receptacle for depositing and withdrawing said bills;

a first storage means for storing said bills;

transport means for transferring said bills from/to said receptacle, said transport means including a transport path for said bills;

sterilizing means for heat-sterilizing said bills;

first transfer means for transferring said bills between said transport path and said first storage means; and second transfer means for transferring said bills between said transport path and said sterilizing means, wherein said sterilizing means and said first storage means are arranged in said cash transaction machine in respective positions along one said of said transport path.

47. A cash transaction machine for performing receiving transactions and/or paying transactions of bills by a user's manipulation, comprising:

a receptacle for depositing and withdrawing said bills;

a first storage means for storing said bills;

transport mean for transferring said bills from/to said receptacle, said transport means including a transport path for said bills;

heating means for heating said bills;

first transfer means for transferring said bills between said transport path and said first storage means; and second transfer means for transferring said bills between said transport path and said heating means, wherein said heating means and said first storage means are arranged in said cash transaction machine in respective positions along one side of said transport path.

48. A cash transaction machine for performing receiving transactions and/or paying transactions of bills by a user's manipulation, comprising:

a receptacle for depositing and withdrawing said bills;

a first storage means for storing said bills;

transport means for transferring said bills between said receptacle and said first storage means, said transport means including a transport path for said bills;

sterilizing means for heat-sterilizing said bills; and transfer means for transferring said bills between said transport path and said sterilizing means, wherein said sterilizing means and said first storage means are arranged in said cash transaction machine in respective positions along one side of said transport path, and wherein said transport path includes gate means which can be switched to allow or not to allow the bills to be transferred between said transport path and said transfer means in accordance with whether the bills should be sterilized or not.

49. A cash transaction machine for performing receiving transactions and/or paying transactions of bills by a user's manipulation, comprising:

a receptacle for depositing and withdrawing said bills;

a first storage means for storing said bills;

transport means for transferring said bills between said receptacle and said first storage means, said transport means including a transport path for said bills;

heating means for heating said bills; and transfer means for transferring said bills between said transport path and said heating means, wherein said heating means and said first storage means are arranged in said cash transaction machine in respective positions along one side of said transport path, and wherein said transport path includes gate means which can be switched to allow or not to allow the bills to be transferred between said transport path and said transfer means in accordance with whether the bills should be sterilized or not.

\* \* \* \* \*